(12) United States Patent
Van der Helm et al.

(10) Patent No.: US 9,078,965 B2
(45) Date of Patent: Jul. 14, 2015

(54) ADMINISTRATION DEVICE HAVING PATIENT STATE MONITOR

(75) Inventors: Wim Van der Helm, Hausen am Albis (CH); Axel Remde, Lutzelfluh (CH); Kurt Friedli, Lyssach (CH)

(73) Assignee: Roche Diagnostics International AG, Rotkreuz (CH)

( * ) Notice: Subject to any disclaimer, the term of this patent is extended or adjusted under 35 U.S.C. 154(b) by 631 days.

(21) Appl. No.: 12/901,090

(22) Filed: Oct. 8, 2010

(65) Prior Publication Data

US 2011/0082445 A1    Apr. 7, 2011

Related U.S. Application Data

(63) Continuation of application No. PCT/EP2009/002586, filed on Apr. 8, 2009.

(30) Foreign Application Priority Data

Apr. 11, 2008  (EP) ..................................... 08007186

(51) Int. Cl.
*A61M 5/142* (2006.01)
*A61M 5/172* (2006.01)

(52) U.S. Cl.
CPC .......... *A61M 5/14244* (2013.01); *A61M 5/1723* (2013.01); *A61M 2205/18* (2013.01); *A61M 2205/332* (2013.01); *A61M 2230/63* (2013.01)

(58) Field of Classification Search
CPC .......... A61M 5/14244; A61M 5/1723; A61M 2205/18; A61M 2205/332; A61M 2230/63
USPC ............. 604/890.1, 65, 66, 67, 131, 151, 245
See application file for complete search history.

(56) References Cited

U.S. PATENT DOCUMENTS

| 6,878,132 | B2 | 4/2005 | Kipfer |
| 2004/0144635 | A1* | 7/2004 | Fitzgerald et al. ............ 200/512 |
| 2005/0043675 | A1 | 2/2005 | Pastore et al. |
| 2006/0173406 | A1* | 8/2006 | Hayes et al. .................... 604/67 |

FOREIGN PATENT DOCUMENTS

| EP | 1124600 B1 | 2/2005 |
| EP | 0991440 B1 | 6/2005 |

(Continued)

OTHER PUBLICATIONS

International Search Report and Written Opinion, Application No. PCT/EP2009/002586 filed Aug. 4, 2009, completion of ISR is Jul. 28, 2009, pp. 1-13.

*Primary Examiner* — Kevin C Sirmons
*Assistant Examiner* — Shefali Patel
(74) *Attorney, Agent, or Firm* — Dinsmore & Shohl LLP

(57) ABSTRACT

Embodiments disclosed herein include systems and methods for administering a drug over a time period. One embodiment of a system includes an administration unit, a housing that houses the administration unit, and a controller unit adapted to receive an alarm triggering signal. Also included in some embodiments is an alarming unit that is adapted to generate an alarm signal on reception of the alarm triggering signal. Some embodiments include a patient state monitor that includes a motion-sensitive sensor unit that is reactive on patient motion. The patient state monitor may be adapted to process a sensor signal generated by the motion-sensitive sensor unit. The patient state monitor may also be adapted to transmit the alarm triggering signal to the controller unit if a patient motion level is below a predefined motion level, as determined by a length of time without patient motion.

15 Claims, 8 Drawing Sheets

(56) References Cited

FOREIGN PATENT DOCUMENTS

| WO | 0158511 | A1 | 8/2001 |
| WO | 2006075016 | A1 | 7/2006 |
| WO | WO 2006075016 | A1 * | 7/2006 |
| WO | 2007138154 | A1 | 12/2007 |
| WO | 2008067314 | A2 | 6/2008 |

* cited by examiner

ADMINISTRATION DEVICE HAVING PATIENT STATE MONITOR

CROSS REFERENCE TO RELATED APPLICATIONS

The present application is a Continuation of International Application No. PCT/EP2009/002586, filed Apr. 8, 2009, which claims priority to EP Application number 08007186.3, filed Apr. 11, 2008, which are each incorporated by reference in their entireties.

TECHNICAL FIELD

Embodiments disclosed herein relate to an administration device for the continuous or quasi-continuous administration of a liquid drug over an extended time period and to a method for supervising such an administration device.

BACKGROUND

Continuous Subcutaneous Insulin Infusion (CSII) is the basis for a state-of-the-art therapy of insulin-dependent diabetes mellitus. In this therapy, a diabetic patient carries a miniaturized infusion pump night and day and preferably concealed from view. The infusion pump administers insulin by a cannula, (the cannula oftentimes being made from medical-grade stainless steel or Teflon), into the subcutaneous tissue. The insulin pump administers insulin in a continuous or quasi-continuous way according to a patient-specific and time-of-day dependent basal profile in order to cover the patient's basal (i.e., meal-independent) insulin need. In addition, the pump is adapted to administer comparatively large insulin boli on demand which are required for covering the intake of food, namely carbohydrates, and to correct for undesirably high blood glucose values. Infusion devices which are adapted for the CSII therapy of diabetes mellitus are disclosed.

A general concern associated with the diabetes therapy based on insulin administration is the danger of hypoglycemia. While the number of potential reasons for this phenomenon is high, it is usually associated with a mismatch between blood glucose level and blood insulin level, with the blood insulin level being too high. The effect of hypoglycemic conditions may vary from a lack of concentration to severe perceptual disturbances, to coma and finally to death. Under normal circumstances, the immediate intake of fast-acting carbohydrates is a sufficient measure. However, in some cases, a diabetic may fall into a hypoglycemic coma very fast without having a chance to act properly.

In a situation of hypoglycemic coma, it is highly desirable to provide an alarm signal in order to get emergency support as fast as possible. It is further desirable to stop drug administration almost immediately in order to not worsen the situation. Therefore, state-of-the-art insulin pumps may comprise a 'dead man's control, which automatically triggers the generation of an audible alarm signal and stops insulin administration if no user interaction with the pump has occurred for a given alarming time in which a user interaction, such as a bolus administration, can be assumed to occur. In order to avoid false alarms, the alarming time may, for example, be as along as 12 hours. This is, however, often found to be inappropriate in different ways. On the one hand, the alarming time may be too short. When sleeping longer than normal (e.g., during the weekend), even a rather long alarming time may be too short and cause false alarms. Such false alarms are generally inconvenient and are even found to be dangerous if insulin administration is stopped due to a false alarm. On the other hand, the alarming time may be too long. If the situation of a hypoglycemic coma occurs shortly after a user interaction, alarming and potentially stopping the insulin administration are triggered only with a delay of many hours.

SUMMARY

Embodiments disclosed herein include systems and methods for administering a drug over a time period. One embodiment of a system includes an administration unit, a housing that houses the administration unit, and a controller unit adapted to receive an alarm triggering signal. Also included in some embodiments is an alarming unit that is adapted to generate an alarm signal on reception of the alarm triggering signal. Some embodiments include a patient state monitor that includes a motion-sensitive sensor unit that is reactive on patient motion. The patient state monitor may be adapted to process a sensor signal generated by the motion-sensitive sensor unit. The patient state monitor may also be adapted to transmit an alarm triggering signal to the controller unit if a patient motion level is below a predefined motion level, as determined by the length of time without patient motion.

Similarly, embodiments of a method may include providing an administration device that is adapted to be carried by a patient, the administration device being further adapted for drug administration over an extended period of time, the administration device including a motion-sensitive sensor unit, the motion sensitive sensor unit being reactive on patient motion, processing a sensor signal (SS) generated by the motion-sensitive sensor unit. Additionally, embodiments of the method may include generating an alarm triggering signal if processing of the sensor signal (SS) indicates a patient motion level below a predefined motion level, the predefined motion level being defined by the length of time-periods without patient motion that can be expected for a conscious human.

BRIEF DESCRIPTION OF THE DRAWINGS

In the following, exemplary embodiments of administration devices according to the present disclosure and exemplary embodiments of methods for detecting a patient motion level below a predefined motion level according to the present disclosure are described in greater detail with reference to the figures.

DETAILED DESCRIPTION

Figure 1:
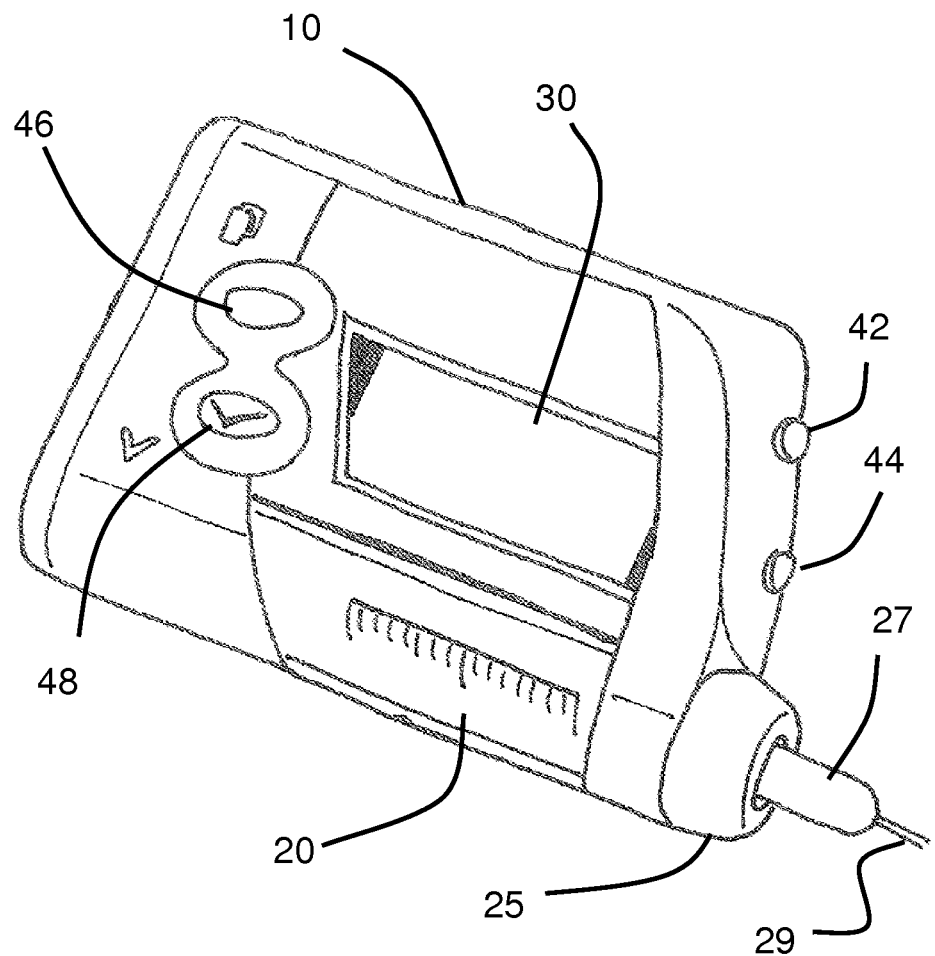
FIG. 1 depicts an administration device according to one or more embodiments shown and described herein.

Embodiments disclosed herein provide administration devices for the continuous or quasi-continuous administration of liquid drugs, such as insulin. These embodiments may be configured to ensure a short delay time for alarming an emergency of a coma patient, while avoiding false alarms. Embodiments disclosed herein may consider patient motion, assuming that a patient is likely to be in a coma if patient motion is below a predefined motion level.

In the following, some terms are defined as they are used in the context of the present disclosure:

The term 'motion-sensitive sensor unit' includes sensor units that are reactive on motion. A motion-sensitive sensor unit may temporarily generate a sensor signal (SS) as a consequence of motion and/or change of motion, such as an acceleration sensor. Alternatively or additionally, the motion sensitive sensor unit may continuously generate a sensor signal (SS) that is changed or modified by motion, such as tilt sensor, the tilt sensor generating a sensor signal (SS) independent of the orientation of a measurement vector with respect to gravity.

The term 'sensor unit' includes both a single sensor as well an arrangement of multiple sensors. For example, one embodiment of a sensor unit may include at least two single acceleration sensors, with each single sensor being associated with a different measurement vector. In such an arrangement, the single sensors may operate according to one or more physical principle. Accordingly, the sensor signal (SS) may include a single signal or a vector of multiple signals.

The term 'derived' in the context of a signal may generally refer to a signal that is obtained from another primary signal by processing such as amplifying, threshold detection, analog-to-digital conversion, filtering, or the like. A derived signal may also be identical with the corresponding primary signal.

The term 'patient motion level' generally refers to an amount of patient motion over time. Patient motion may be assessed based on diverse criteria such peak acceleration values, average acceleration values, mean time between consecutive patient motions, duration of continuous patient motions, duration of time intervals without patient motion, or the like.

Accordingly, embodiments of an administration device for the administration of a liquid drug over an extended time period to a patient, include an administration unit, a housing that includes the administration unit. In some embodiments, the housing is adapted to be carried by a patient over an extend time period. Also included in some embodiments is a controller unit that controls operation of the administration unit and receives an alarm triggering signal, at least one alarming unit. The at least one alarming unit may be coupled to the controller unit and adapted to generate at least one alarm signal on reception of the alarm triggering signal by the controller unit.

Similarly, some embodiments of an administration device include a patient state monitor that includes a motion-sensitive sensor unit. The motion-sensitive senor unit may be reactive on patient motion. Similarly, the patient state monitor may be adapted to process a sensor signal (SS) that is generated by the motion-sensitive sensor unit and adapted to generate an alarm triggering signal. The patient state monitor may also be adapted to transmit the alarm triggering signal to the controller unit if processing of the sensor signal (SS) indicates a patient motion level below a predefined motion level, the predefined motion level being defined by the length of time-periods without patient motion that can be expected for a conscious human.

Similarly, some embodiments of an administration device for the administration of a liquid drug over an extended time period according to the present disclosure include an administration unit and a housing that includes the administration unit and is adapted to be carried by a patient over an extend time period. The administration device may also include a controller unit that is adapted to control operation of the administration unit and to receive an alarm triggering signal. The administration device may also include at least one alarming unit that is coupled to the controller unit and adapted to generate at least one alarm signal on reception of the alarm triggering signal by the controller unit. Some embodiments include a patient state monitor that includes a motion-sensitive sensor unit that is reactive on patient motion. The patient state monitor may be adapted to process a sensor signal (SS) that is generated by the motion-sensitive sensor unit. Similarly, the patient state monitor may be adapted to generate an alarm triggering signal and to transmit the alarm triggering signal to the controller unit if processing of the sensor signal (SS) indicates a patient motion level below a predefined motion level, where the predefined motion level is defined by the length of time-periods without patient motion that can be expected for a conscious human.

In some embodiments, the administration device includes additional elements, such as a drug reservoir, a user interface, a power supply, at least one data interface. Similarly, in some embodiments disclosed herein the controller unit may include elements such as such as application specific integrated circuits (ASICs), micro controllers, memory circuits, clock and timer circuits, general digital and analog circuitry, and the like. The controller unit may also include at least one micro controller.

Similarly, in some embodiments, the alarming unit includes at least one of an audio alarm generator (such as a buzzer or loud speaker) and a tactile alarm generator (such as a pager vibrator). Further, in some embodiments, the at least one alarming unit is included in the housing. Alternatively or additionally, the alarming unit may include remote alarm generators, such as dedicated alarming devices carried by a third person. In some embodiments, the at least one alarming unit further serves as indication unit for general control and operation feedback purposes.

In still some embodiments, components of the administration device may include and/or coupled to the housing. In some embodiments, however, some components include and/or are coupled to a least one additional housing. For example, the controller unit may, totally or in part, be included within an additional controller housing, where the controller unit and the administration unit are adapted for wireless communication. Similarly, a user interface may, totally or in part, be provided by a user interface housing, the user interface housing being separate from the housing, in order to enable convenient and discrete operation. Further housings may be provided if the housing is adapted to be attached substantially directly at the infusion site, (e.g., as a patch or further locations that can not guaranteed to be accessible in an easy and discrete way for user interaction purposes).

According to some embodiments, the patient state monitor includes a motion-sensitive sensor unit. Similarly, the patient state monitor may include further elements such as signal conditioning circuitry, counters, timers, shift registers, energy storages, or the like as described in grater detail below in the framework of exemplary embodiments. The patient state monitor may, at least in part, be integral with the controller unit.

In some embodiments, the motion-sensitive sensor unit may be rigidly coupled to the housing. For this kind of design, any motion of the housing is directly transferred to the motion-sensitive sensor unit. Similarly, in some embodiments, the motion-sensitive sensor unit is included within and/or coupled to a motion sensor housing, the motion sensor housing being separate from the housing.

In some embodiments, the motion-sensitive sensor unit is included within and/or coupled to a motion sensor unit housing, the motion sensor unit housing being separate from the housing. For example, the motion-sensitive sensor unit may be included with and/or rigidly coupled to a dedicated motion sensor unit housing, the motion sensor unit housing being adapted to be carried, (e.g., as a wrist watch is carried).

Besides the motion-sensitive sensor unit, the motion sensor unit housing may include additional elements of the patient state monitor. The motion sensor unit housing may include a wireless motion sensor unit data interface, where the motion sensor unit data interface is operatively coupled to the motion-sensitive sensor unit. In such embodiments, the motion sensor unit data interface may be adapted to transmit the sensor signal (SS) and/or at least one signal derived from the sensor signal (SS). Providing a dedicated motion sensor unit housing such as a wrist watch like motion sensor unit housing allows coupling of the motion-sensitive sensor unit to a patient's arm or leg, which are typically more likely to move than the patient's body, especially while sleeping.

In some embodiments of the administration device, the motion-sensitive sensor unit includes at least one of a tilt sensor, a vibration sensor, a shock sensor, and an acceleration sensor. Similarly, in some embodiments, the motion-sensitive sensor unit includes at least one of a tilt sensor, a vibration sensor, a shock sensor, and an acceleration sensor. In further embodiments, other kinds of motion-sensitive sensors, such as gyroscopic sensors, are used. Additionally, in some embodiments, the motion-sensitive sensor unit includes at least one binary switching sensor, such as an acceleration switch, a vibration switch or a tilt switch. The corresponding sensor signal (SS) reflects the state of the sensor, (i.e., 'open' or closed').

Similarly, some embodiments include at least two binary switching sensors that have different measurement axes. The measurement axes may be substantially perpendicular to each other. The at least two binary switching sensors may be electrically parallel to form a resulting switch, the resulting switch being closed if at least one of the binary switching sensors is closed.

In some embodiments, the motion-sensitive sensor unit includes at least one sensor generating a quantitative sensor signal (SS), such as a piezo acceleration sensor, a capacitive acceleration sensor or a gyroscopic sensor. If the motion-sensitive sensor unit includes a piezo electric acceleration sensor, a charge amplifier circuit may be used for charge-to-voltage conversion purposes, thereby allowing the quantitative evaluation of acceleration in addition to the qualitative detection of patient motion. Since embodiments disclosed herein may be configured to detect the occurrence of substantial patient motion, a charge-generating piezo electric sensor may also be directly coupled to an analog-to-digital conversion circuit such as a Schmitt trigger or the like, in order to obtain a binary signal.

According to some embodiments that include a motion-sensitive sensor unit comprising at least two single motion-sensitive sensors, the signals generated by the at least two motion-sensitive sensors are, at least in part, evaluated independently. Providing a motion-sensitive sensor unit comprising at least two single motion-sensitive sensors is especially advantageous in order to avoid false alarms because of patient motions not being detected by a motion-sensitive sensor having one fixed measurement axis. Similarly, in some embodiments, the patient state monitor includes an energy storage and is adapted to modify an energy (E) stored by the energy storage.

In some embodiments, the patient state monitor includes an energy storage and the motion-sensitive sensor unit that is adapted to modify an energy (E) is stored by the energy storage. Similarly, in some embodiments, the energy storage includes a capacitor and the energy (E) is stored in the electrical field of the capacitor. Similarly, other types of energy storages such as coils or mechanical springs may be used as energy storage. In some embodiments that include a capacitor as energy storage, the motion-sensitive sensor unit includes at least one binary switching sensor, where closing the at least one binary switching sensor results in fully or partly charging or discharging the capacitor. Similarly, in some embodiments, the controller unit is adapted to control the administration unit to stop drug administration on reception of the alarm triggering signal.

Further, in some embodiments, the controller unit may be adapted to control the administration unit to stop drug administration on reception of the alarm triggering signal. Stopping drug administration may be desirable, such as in the framework of diabetes therapy by CSII in order not to worsen the situation in case of a hypoglycemic coma. The patient state monitor may include a counter that is adapted to count a number N of consecutive monitoring intervals without substantive patient motion. In still some embodiments, the patient state monitor is adapted to generate an alarm triggering signal if the counter state N equals a threshold number (TN).

In some embodiments disclosed herein, the patient state monitor is adapted to be selectively deactivated. Similarly, the patient state monitor may be automatically deactivated for given periods of time per day and/or for given days of a week. For example, the patient state monitor may be automatically deactivated during night time in order to avoid false alarms. The patient state monitor may also be adapted for manually deactivation by the patient for a given time interval and/or until a given time of day. In some embodiments, the patient state monitor is further adapted to be fully deactivated by the patient and/or a healthcare professional. A patient state monitor may also be included that is adapted to be selectively deactivated. The administration device may further include a dead man's control unit, that is adapted to be activated upon deactivation of the patient state monitor. A dead man's control unit may further be provided in addition to the patient state monitor for safety and redundancy purposes.

In some embodiments, the patient state monitor is, at least in part, adapted to be discontinuously energized. In the context of applications such as diabetes therapy by CSII, power consumption is generally critical as the power supply is one of the major components determining the administration device size. In some embodiments, the patient state monitor is, at least in part, adapted to be energized only for defined sampling points in time and/or during given sampling intervals and may be de-energized otherwise. The sensor signal generated by the motion-sensitive sensor unit is preferably not processed if the patient-state monitor is, at least in part, de-energized.

Discontinuously energizing may affect the patient state monitor as a whole or may affect only some power consuming components of the patient state monitor, such as the motion-sensitive senor and signal condition circuitry, while not affecting other components such as counters.

Also disclosed herein are embodiments of a method for detecting a patient motion level below a predefined motion level. Such a method for detecting a patient motion level below a predefined motion level in accordance with the present disclosure may especially be utilized for supervising an administration device according to the present disclosure as described above.

More specifically, disclosed herein are embodiments of a method for detecting patient motion below a predefined motion level. Such embodiments may include providing an administration device that is adapted to be carried by a patient and for drug administration over an extended period of time. The administration device may include a motion-sensitive senor unit that is reactive on patient motion. Similarly, some embodiments include processing a sensor signal (SS) generated by the motion-sensitive sensor unit and generating an alarm triggering signal if processing of the sensor signal (SS) indicates a patient motion level below a predefined motion level, the predefined motion level being defined by the length of time-periods without patient motion that can be expected for a conscious human.

Similarly, some embodiments of a method for detecting a patient motion level below a predefined motion level may include providing an administration device, the administration device being adapted to be carried by a patient and for drug administration over an extended period of time. The administration device may include a motion-sensitive sensor unit and may be reactive on patient motion. The method may also include processing a sensor signal (SS) generated by the motion-sensitive sensor unit and generating an alarm triggering signal if processing of the sensor signal (SS) indicates a patient motion level below a predefined motion level. The predefined motion level may be defined by the length of time-periods without patient motion that can be expected for a conscious human. It should be understood that the predefined motion level may be given by a minimum motion level that can be expected by a conscious human. A predefined motion level may be different for different patients, for different situations, for different times of day (e.g., for daytime and nighttime), and so on.

Similarly, in some embodiments, the predefined motion level may be defined by length of time periods without patient motion and the method includes generating an alarm triggering signal if processing of the sensor signal (SS) indicates no patient motion for a given alarming time interval (AT). For this kind of embodiment, the predefined motion level is given by the alarming time period AT. In some embodiments, the method further includes the step of generating at least one alarm signal upon generation of the alarm triggering signal.

Some embodiments of the method may include providing monitoring intervals and counting a number N of consecutive monitoring intervals without substantive patient motion. The method may also include generating an alarm trigger signal if the number N equals a threshold number N, as described below.

In some embodiments that include generation of at least one alarm signal, the at least one alarm signal may include at least one of an audible alarm signal and a tactile alarm signal. The at least one alarm signal may be generated by at least one alarming unit, where the at least one alarming unit is included with and/or coupled to the administration device. In some embodiments, the alarm signal may be generated remotely, (e.g., by an alarming unit comprised by a remote controller). In some embodiments, the alarm signal may be generated by commercial devices such as a cell phone carried by a health care professional and/or a person other than the patient. Similarly, some embodiments include modifying the predefined motion level.

Some embodiments of the method include modifying the predefined motion level. More specifically, some embodiments involve an alarming time interval (AT), where the method comprises modifying the alarming time interval (AT) by a patient and/or a healthcare professional in order to adopt the alarming time interval (AT) to the patient's individual situation and life style. For example, for a patient being a craftsman, a much shorter alarming time interval (AT) may be appropriate as compared to an office worker who typically spends several hours sitting at a desk with very little motion. Similarly, in some embodiments, a set of at least two different predefined motion levels is provided and the method comprises manually or automatically selecting either of the at least two motion predefined levels.

In still some embodiments, the method includes modifying the predefined motion level based on at least one of the following: time of day, day of week, and past patient motion. More specifically, some such embodiments include modifying the predefined motion level based on at least one of time of day, day of week, and past patient motion. For example, embodiments of the method may involve an alarming time interval (AT), and include automatically switching the alarming time interval (AT) between a first alarming time during daytime and a second alarming time during night time, the second alarming time being larger than the first alarming time. In this way, a short alarming delay may be achieved during the daytime where a lot of patient motion may occur without causing false alarms during night time and especially during sleep where less patient motion is likely to occur. Similarly, the alarming time interval (AT) may be automatically modified to be different for working days and weekend days.

In some embodiments, the predefined motion level may be modified based on past patient motion. For example, if a diabetic person is newly equipped with an administration device according to embodiments of the present disclosure, the alarming time interval (AT) may first be set to a comparatively long default value of, for example, 6 hours. Subsequently, the sensor signal (SS) may be processed and evaluated for an adoption time interval of, for example, 1 month in order to determine the patient's individual motion habits and motion level. The initial alarming time may subsequently be modified based on the longest time interval without substantial patient motion within the adoption time interval or based on a quartile, such as the 95% quartile of all periods of time without substantial patient motion within the adoption time interval. In addition to or alternatively to providing a dedicated adoption time interval, the patient motion level may be monitored and the predefined motion level may be configured to automatically adapt the predefined motion level to change in circumstances such as a change from work to holidays and vice versa and/or changes in habits or lifestyle of the patient.

Further, some embodiments of the method include sampling a patient state signal (PS), the patient state signal (PS) being identical with and/or derived from the sensor signal (SS) at defined sampling points in times, the sampling points in time defining monitoring intervals. Further, some embodiments include sampling a patient state signal, the patient state signal being identical to or being derived from the sensor signal (SS) at defined sampling points in times, the sampling points in time defining monitoring intervals. An alarming time interval (AT) may be defined by the product of the monitoring interval length MT and a threshold number (TN), such that an alarm triggering signal is generated if the patient has not moved for TN consecutive monitoring intervals.

In some embodiments, the sensor signal (SS) is continuous and is changed or modified as a result of patient motion, such as the signal generated by a tilt sensor. In this case, embodiments of the method may include assuming that the patient has not moved within a given monitoring interval if the patient state signal (PS) is substantially identical at the two consecutive sampling points in time bordering the given monitoring interval. If for example, the motion-sensitive sensor unit includes a tilt switch, the method may include assuming that the patient has not moved within a given monitoring interval if the tilt switch is open at both of the two consecutive sampling points in time bordering the given monitoring interval or is closed at both of the consecutive sampling points in time bordering the given monitoring interval.

In still some embodiments, the sensor signal (SS) is generated temporarily as a direct consequence of patient motion and/or change of patient motion, such as the signal generated by an acceleration sensor. In this case, the method may include modifying the patient state signal (PS) based on the sensor signal (SS) during a monitoring period and sampling the patient stat signal at the monitoring points in time. Embodiments also include sampling a patient state signal (PS) at defined monitoring points in time, the monitoring points in time defining monitoring intervals, is especially advantageous with respect to energy consumption in contrast to sampling a patient state signal (PS) continuously. Additionally, some embodiments may include modifying the energy (E) stored in an energy storage, wherein modifying the energy (E) is triggered by patient motion.

In still some embodiments, the method comprises modifying the energy (E) stored in an energy storage, wherein modifying the energy (E) is, at least in part, triggered by patient motion. The patient state signal (PS) may be correlated with the energy (E). In some embodiments, the method includes modifying the energy (E) to change between a first energy E_1 and a second energy E_2, where the first energy E_1 is different than the second energy. In still embodiments, the method includes modifying the energy (E) stored by a capacitor, the capacitor making up the energy storage and the capacitor voltage U_C making up the patient state signal (PS). In embodiments involving an alarming time interval (AT), where the alarming time interval (AT) is defined by the product of a monitoring interval length and a threshold number (TN), the motion-sensitive sensor may include an acceleration switch.

Similarly, embodiments of the method may include sampling the capacitor voltage U_C and comparing the capacitor voltage U_C with a threshold voltage U_T. If the capacitor voltage U_C is below the threshold voltage U_T, the method may include resetting a counter, the counter counting the number N of consecutive monitoring intervals without substantial patient motion, charging the capacitor to a capacitor voltage U_C=U_0, followed by starting a new monitoring interval, and during the monitoring interval, discharging the capacitor to a voltage U_C=0 if the acceleration switch is closed. Similarly, some embodiments include continuing with sampling the capacitor at the end of the monitoring interval.

If the capacitor voltage U_C is above the threshold voltage U_T, the method may include incrementing the counter state N of the counter by one. Similarly, if the counter state N equals a threshold number (TN), the method may include generating an alarm triggering signal. If the counter state N is lower than the threshold number (TN), the method may include continuing with charging the capacitor.

In embodiments that include sampling a patient state signal (PS), the patient state signal (PS) being identical to and/or derived from the sensor signal (SS), during sampling intervals, the sampling intervals may alternate with non-sampling intervals. Similarly, some embodiments include sampling a patient state signal (PS), where the patient state signal (PS) is identical to or derived from the sensor signal (SS), during sampling intervals, the sampling intervals alternating with non-sampling intervals. During sampling interval, embodiments may include sampling the patient state signal (PS) continuously or quasi-continuously. In some embodiments, the sampling interval length (ST) is not constant but is limited not to exceed a maximum sampling interval length (ST)_max, while the non-sampling interval length NST is constant.

Similarly, some embodiments include resetting and starting a sampling timer, the sampling timer measuring the sampling time t during a sampling interval. Some embodiments may include continuously or quasi continuously sampling the patient state signal (PS) until the sampling time t equals the maximum sampling interval length (ST)_max or the patient state signal (PS) indicates a substantial patient motion. If the sampling time t does not equal the maximum sampling interval length (ST)_max, embodiments may include stopping the sampling timer and waiting for a non-sampling interval, the non sampling interval having a given non sampling interval length NST, followed by continuing with resetting and sampling the sampling timer. If the sampling time t equals the maximum sampling interval length (ST)_max, generating an alarm triggering signal.

For such embodiments, the predefined motion level may be defined by a maximum time without patient motion and an alarming time interval (AT) may be given by the sum of the maximum sampling interval length (ST)_max and the non sampling interval length NST. The maximum sampling interval length (ST)_max may be chosen such that at least one patient motion occurs during a sampling interval if the patient is not in a coma. For example, the non-sampling interval length NST may be chosen to be 15 minutes and the maximum sampling interval length (ST)_max may be chosen to be 45 minutes, resulting in a an alarming time interval (AT) of 1 hour.

Non-sampling intervals may be utilized to reduce energy consumption. In embodiments comprising non-sampling intervals, embodiments may include energizing a patient state monitor, at least in part, discontinuously. For example, a motion-sensitive sensor unit and additional signal conditioning circuitry may not be energized during non-sampling intervals.

In some embodiments, the method may include controlling an administration unit, the administration unit being comprised by the administration device, to stop drug administration along with generation of the alarm triggering signal. Similarly, the method may also include controlling an administration unit, the administration unit included with the administration device, to stop drug administration along with generation of the alarm triggering signal.

Referring now to the drawings, FIG. 1 depicts an administration device according to exemplary embodiments of the disclosure. Similarly, FIG. 2 reflects the internal structure of an embodiment of the administration device schematically. Such an embodiment may be suited and designed for the insulin administration in the framework of diabetes therapy using CSII and the following description of exemplary embodiments refers to diabetes therapy. In the following, reference is first made to FIG. 1 and to FIG. 2.

The administration device includes a housing 10, the housing 10 enclosing the other device components. The housing 10 is adapted to be worn by a patient during both night and day and is adapted to be carried without attracting attention (e.g., in a belt holster). The administration device may further be carried concealed from view, such as in a trousers pocket, as a necklace, or the like.

The administration device includes a drug reservoir 20, an infusion line 27, 29 and an infusion line adapter 25, the infusion line adapter 25 coupling the infusion line 29 to the drug reservoir 20. The housing 10, the drug reservoir 20 and the infusion line adapter 25 are designed to form a sealed and watertight unit in the assembled state shown in FIG. 1. The infusion line 29 is connected to an infusion cannula (not visible in the figures). The infusion cannula is placed in the subcutaneous tissue and is replaced by the patient every few days. The drug reservoir 20 may, for example, hold 3.15 ml of insulin, with each ml of insulin corresponding to 100 International Units (IU) of insulin.

Figure 2:
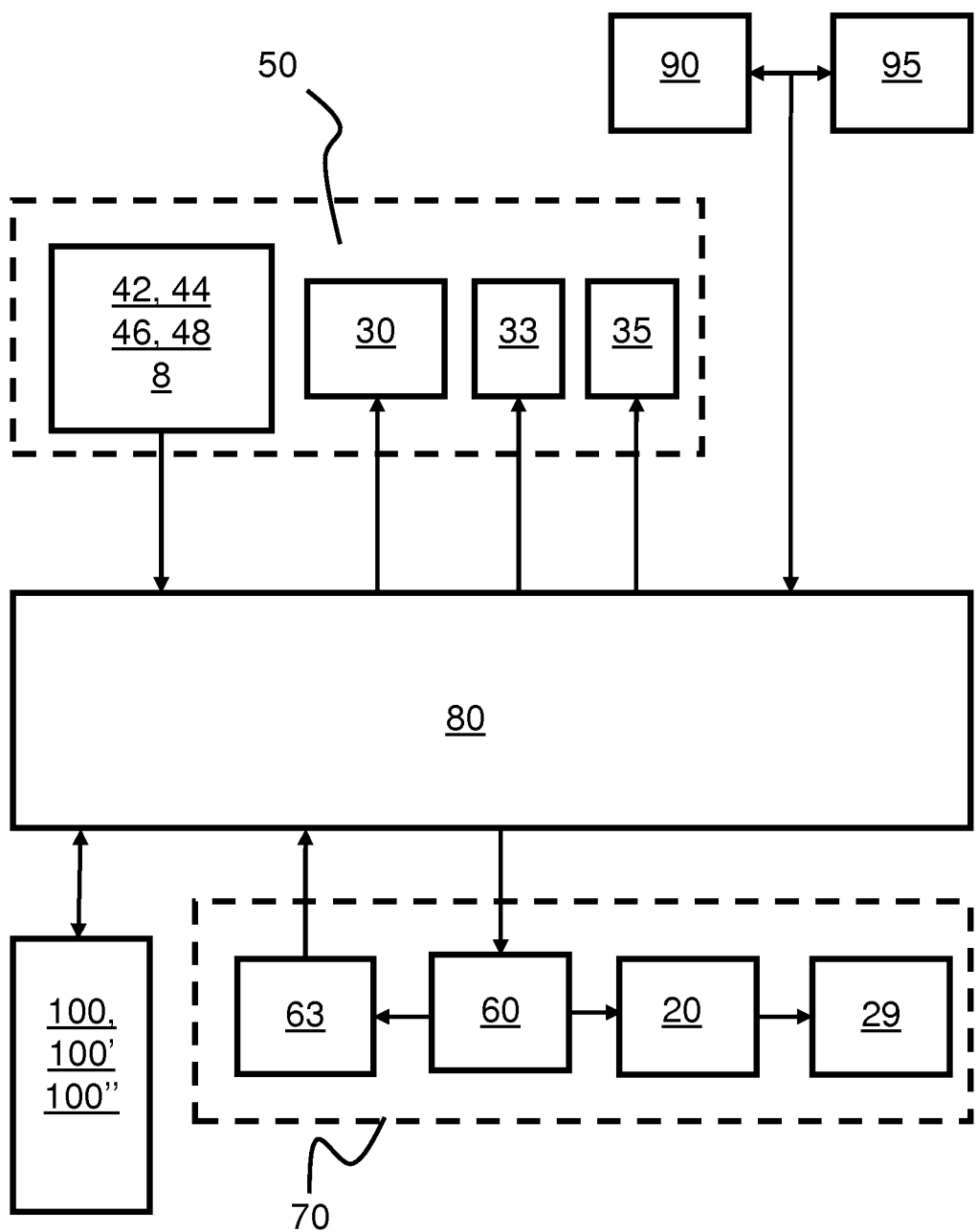
FIG. 2 depicts an internal functional structure of an exemplary administration device, such as shown in FIG. 1.

Referring now to FIG. 2, the exemplary administration devices include a user interface 50, the user interface 50 comprising four pushbuttons 42, 44, 46, 48, a display 30, an alarming unit 33 in form of a buzzer and a alarming unit 35 in form of a pager vibrator. The display 30 is a graphical Liquid Crystal Display (LCD) and is used to provide information that is utilized for this kind of device, such as operation mode information, time and date, drug bolus information, current basal infusion rate information, menu items for programming the administration device, alerts and error messages, and the like. The alarming unit 33 and the alarming unit 35 are provided for generating non-visual user feedback signals and further serve as alarming unit.

For performing the drug administration, a pump unit 60 and a supervision unit 63 are provided. In this exemplary embodiment, the pump unit 60 includes a motor-driven spindle drive and the supervision unit 63 includes a force sensor and a rotary encoder. In combination, the drug reservoir 20 (FIG. 1), the pump unit 60 and the supervision unit 63 form the administration unit 70. Several suitable designs for the pump unit 60 may be designed.

The operation of the administration device is controlled by the controller unit 80. The Controller unit 80 is realized as an electronics circuit and includes all the elements typically comprised by the control circuit of this kind of administration devices, such as one or multiple micro controllers, static and dynamic memory, a clock circuit, a power circuit for controlling the pump unit 60, safety circuits, and the like. The controller unit 80 is connected to a power supply such as a rechargeable or non-rechargeable battery.

The administration device further comprises two bidirectional data interfaces, namely an infrared (IR) data interface 90 and an Radio Frequency RF data interface 95, according, e.g., to the BLUETOOTH™ standard for multiple configuration, remote control and data exchange purposes which are typical for this kind of device.

The exemplary administration device further comprises a patient state monitor 100, 100', 100". While both the structure of the patient state monitor 100, 100', 100" and the method detecting a patient-motion level below a predefined motion level are in part dependent on the specific embodiment of the patient state monitor 100, 100', 100", the general design of the administration device as shown in FIG. 1 and FIG. 2 and as described above may be identical for all exemplary embodiments of this disclosure. In addition, it will be understood that the exemplary embodiments of the patient state monitor 100, 100' and the exemplary methods for controlling the operation of the administration device are not limited to administration devices of this specific structure.

It should be noted that the patient state monitor 100, 100', 100" is shown separated from the controller unit 80, while the patient state monitor 100, 100', 100" may be partly integral with the controller unit 80 in the technical implementation. The program flow for the operation of the patient state monitor 100, 100', 100" and the program flow for supervising the administration device according to the present disclosure may be considered as part of the general program flow for controlling the administration device. In particular, timing and program flow are generally controlled by the controller unit 80 for all exemplary embodiments described below in greater detail.

Figure 3:
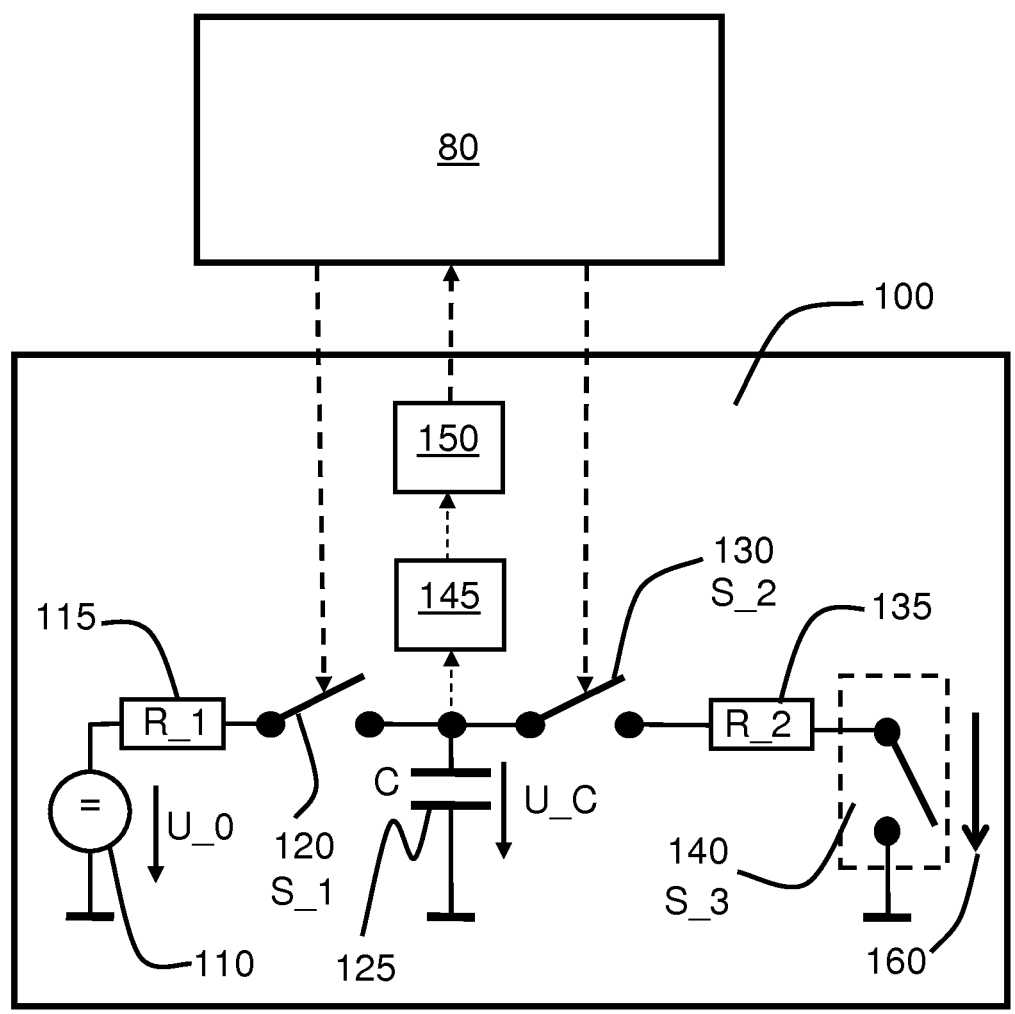
FIG. 3 depicts a schematic structure of an exemplary patient state monitor of an exemplary administration device.

FIG. 3 shows the schematic structure of a patient state monitor 100 according to an exemplary embodiment. In the following, when referring to dedicated electronics components like resistors or switches as such, numeral reference signs are used while alpha numeric reference signs, such as 'R_1', 'S_2', are used to refer to the value of an element such as a resistor, or a state of an element such as a switch.

The patient state monitor 100 includes a constant voltage supply 110 of voltage U_0, a charging resistor 115 of resistance R_1, a capacitor 125 of capacity (C), the capacitor 125 serving as energy storage, a discharging resistor 135 of resistance R2, and an acceleration switch 140, the acceleration switch 140 acting as motion-sensitive sensor unit. Instead of an acceleration switch, other kinds of switches may be used that are normally open and close temporarily due to motion, such as vibration switch or shock switch. The design may further be modified to use switches which are normally closed and open temporarily due to motion.

The patient state monitor 100 further includes a charging switch 120 and a coupling switch 130. The charging switch 120, as well as the coupling switch 130, are controlled by the controller unit 80 and may be realized as solid state semiconductor switches, but may also be realized as electromechanical switches such as micro reed relays. The patient state monitor 100 further includes a voltage threshold detector 145, the voltage threshold detector 145 being operatively coupled to the capacitor 125 and to a counter unit 150. The voltage threshold detector 145 may, for example, be realized as a Schmitt trigger or may be realized by a quantitative analog-to-digital converter, where the digital output of the converter is compared to a corresponding threshold number. The voltage threshold detector 145 may also include additional signal conditioning components such as voltage level converters, filters, or the like.

The acceleration switch 140 is normally open and is closed if it is exposed to an acceleration a in the direction defined by the measurement vector 160, the acceleration a exceeding a given threshold acceleration. Such acceleration switches are, among others, supplied by Assemtech Europe Ltd, UK.

Figure 4:
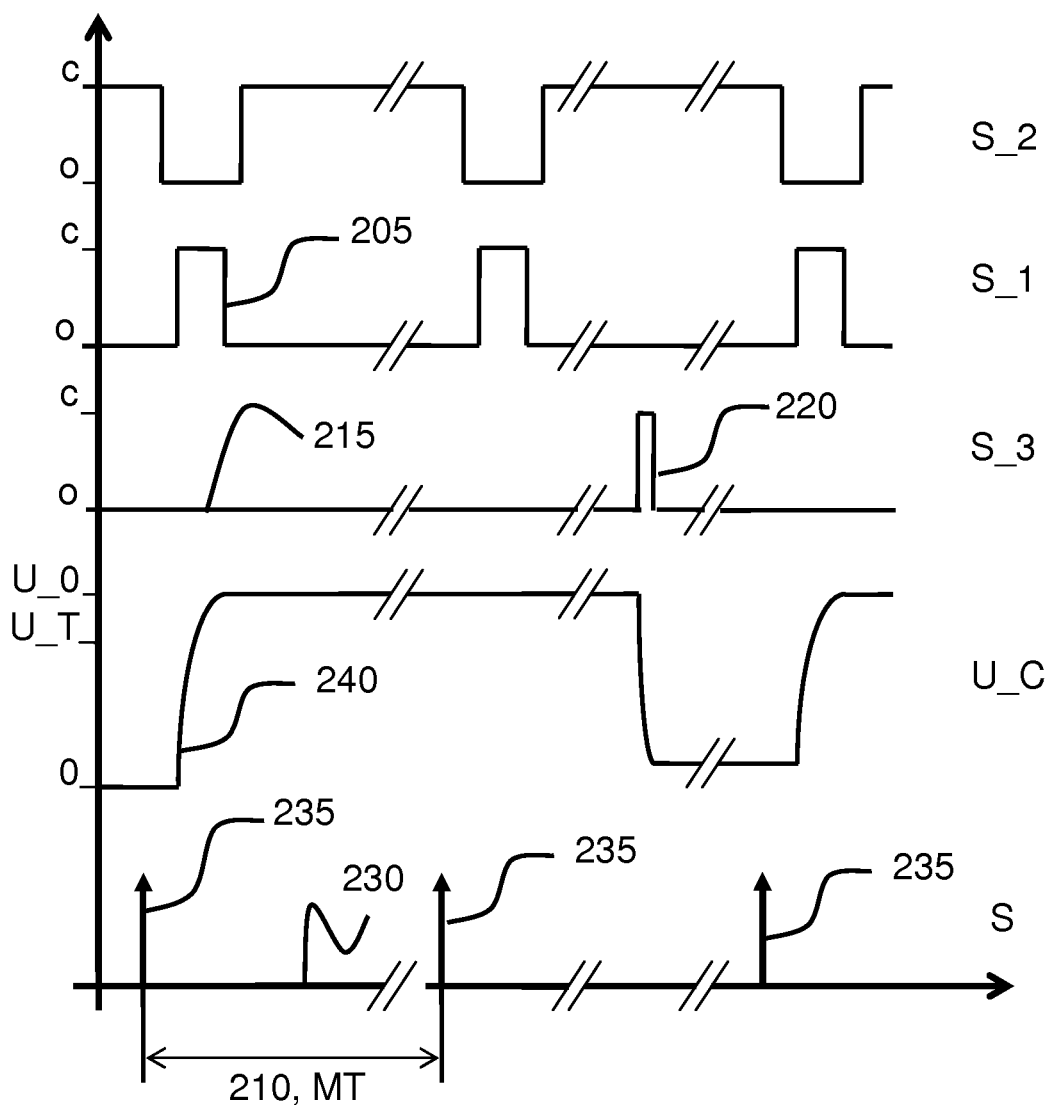
FIG. 4 qualitatively depicts signals as may be probed in a patient state monitor according to FIG. 3.

In the following, operation of the patient state monitor 100 is described with reference to both FIG. 3 and FIG. 4. FIG. 4 qualitatively reflects major signals as may be probed in a patient state monitor 100 according to FIG. 3 as a function of time t. For all switches, 'o' indicates an open switch while 'c' indicates a closed switch. The capacitor 125 is assumed to be fully discharged in an initial state, resulting in the capacitor voltage U_C to be substantially zero. The sensor signal (SS) is made up by the status of the acceleration switch 140 while the patient state signal (PS) is made up be the capacitor voltage U_C.

As indicated by the curve 205, the charging switch 120 is closed periodically, the period defining the monitoring interval 210 of monitoring interval length MT. The closing time of the charging switch 120 is generally short, but is sufficient to charge the capacitor 125 to a capacitor voltage U_C 240, which may be substantially equal to the voltage U_0 via the charging resistor 115, resulting the energy (E) stored by the capacitor to be $E=E\_1=0.5*C*U\_0^2$.

For example, the capacitor 125 may be designed to have a value of C=100 pF while the charging resistor 115 may be designed to have a value of R_1=100 kΩ, resulting in a charging time constant of $\tau\_1=R\_1*C=10$ μsec and the closing time of charging switch 120 may be chosen as $4*\tau\_1$. On the one hand, small values are preferable for both the charging resistor 115 and the capacitor 125 in order to achieve a small charging time constant $\tau\_1$. On the other hand, a small charging current is desirable, resulting in a lower limit for the value R\_1 of the charging resistor 115.

After charging the capacitor 125, and assuming the coupling switch 130 to be closed, closing the acceleration switch 140 results in the capacitor 125 being discharged via the discharging resistor 135, thereby resulting in the capacitor voltage U\_C. Thus, the energy (E) stored by the capacitor 125 after discharging may fall substantially to E=E\_2=0. The dimension of the discharging resistor R\_2 is such that the discharging time constant $\tau\_2=R\_2*C$ is short enough to ensure substantially full discharging of the capacitor 125 if the acceleration switch 140 is closed for a time of some microseconds. With a dimension of the capacitor as given above, the value R\_2 of the discharging resistor 135 may be chosen to 1 kΩ. The purpose of the discharging resistor 135 is to limit the discharging current of the capacitor 125 and may not be required at all if the capacity (C) of the capacitor 125 is sufficiently small and the acceleration switch 140 is designed for the resulting discharging current.

In FIG. 4, curve 215 showing the state of the acceleration switch 140 and the pulse 220 indicates a patient motion. If the patient has not moved within the monitoring interval 210, the capacitor voltage U\_C does not substantially change within the corresponding monitoring interval 210, i.e., it substantially stays at the level U\_0.

As indicated by the curve 'S', 230, the capacitor voltage U\_C 235 is sampled at the beginning of each monitoring interval 210 virtually immediately prior to closing the charging switch 120 and is compared with a threshold voltage U\_T by the voltage threshold detector 145. The threshold voltage U\_T is chosen such that the capacitor voltage U\_C does not fall below the threshold voltage U\_T due to leakage of the capacitor 125 but does certainly fall below the threshold voltage U\_T if at least one patient motion resulting in closing the acceleration switch 140 occurs in the monitoring interval 210. The threshold voltage U\_T may be fixed to, e.g., (0.8 . . . 0.9)*U\_0.

The binary output of the voltage threshold detector 145 is sent to the counter unit 150. The counter unit 150 includes a counter counting the number N of consecutive monitoring intervals without substantial patient motion. A comparator is also included to compare the counter state N with a threshold number (TN). If the patient has moved within the past monitoring interval 210, (for example, if the capacitor voltage U\_C is below the threshold voltage U\_T), the counter is reset to zero, otherwise the number N is incremented by one.

The alarming time interval (AT) is given by the product of the monitoring interval length MT and the threshold number (TN). If no patient motion has occurred for TN consecutive monitoring intervals 210, an alarm triggering signal is generated by the comparator that is included within the counter unit 150 and is transmitted to the controller unit 80. Along with controlling the acoustical indicator 33 and/or the alarming unit 35 to generate alarm signals, a corresponding alarm message is displayed on the display 30 and the administration unit 70 is instructed to stop drug administration. While charging the capacitor 125, the capacitor 125 may be decoupled from the acceleration switch 140 via the coupling switch 130 in order to prevent the capacitor 125 to be charged improperly or incompletely due to a patient motion which may occur during charging.

The monitoring interval length MT may principally be similar (and/or identical) to the alarming time interval (AT), resulting in the TN=1. However, this signifies that the capacitor 125 is virtually free from leakage. The alarming time interval (AT), for example, may be set to a typical value of 1 hour. During this period of time, the capacitor voltage U\_C may fall from U\_0 below U\_T due to leakage even if the acceleration switch is permanently open. The length MT of the monitoring interval 210 is therefore chosen to be substantially shorter than the alarming time interval (AT). Depending on the leakage properties of the capacitor 125, the monitoring interval length may be chosen to be, for example, 3 minutes. This results in the threshold number (TN)=20 for the alarming time interval (AT) being 1 hour. According to a modification of this exemplary embodiment, capacitor leakage is taken into account by successively lowering the threshold voltage U\_T within a monitoring interval such that the capacitor voltage U\_C does not fall below the threshold voltage U\_T within a monitoring interval because of capacitor leakage.

The exemplary embodiment of the patient state monitor 100 as described above may be slightly modified for energy efficiency purposes. Instead of closing the charging switch 120 at the beginning of each monitoring interval 210, it may be closed in order to recharge the capacitor 125 if the capacitor voltage U\_C has fallen below a charging threshold voltage U\_CT. The charging threshold voltage U\_T is selected such that the capacitor voltage U\_C will not fall below the threshold voltage U\_T within the following monitoring interval 210 due to capacitor leakage, with U\_T<U\_CT<U\_0. It should be noted that the patient state monitor 100 of this exemplary embodiment is designed to detect if the patient has moved within a monitoring interval 210.

According to another exemplary embodiment, the capacity (C) of the capacitor 125 is considerably larger such that the capacitor is typically not fully discharged if the acceleration switch is temporarily closed due to a patient motion and the capacitor voltage U\_C is evaluated quantitatively at the beginning of each monitoring interval. In this case, the capacitor voltage U\_C prior to charging is generally either substantially equal to voltage U\_0 nor to substantially equal to zero, but may take any value between zero and U\_C, dependent on how often and how long the acceleration switch 140 was closed during the past monitoring interval due to acceleration. By evaluating the capacitor voltage U\_C, the patient motion level can be assessed quantitatively besides detecting if a patient motion has occurred. In a further modification, the charging switch 120 is not closed for fixed periods of time for charging the capacitor 125, but the capacitor voltage U\_C is sampled during charging and the charging switch 125 is opened when the capacitor 125 is substantially fully charged.

Figure 5:
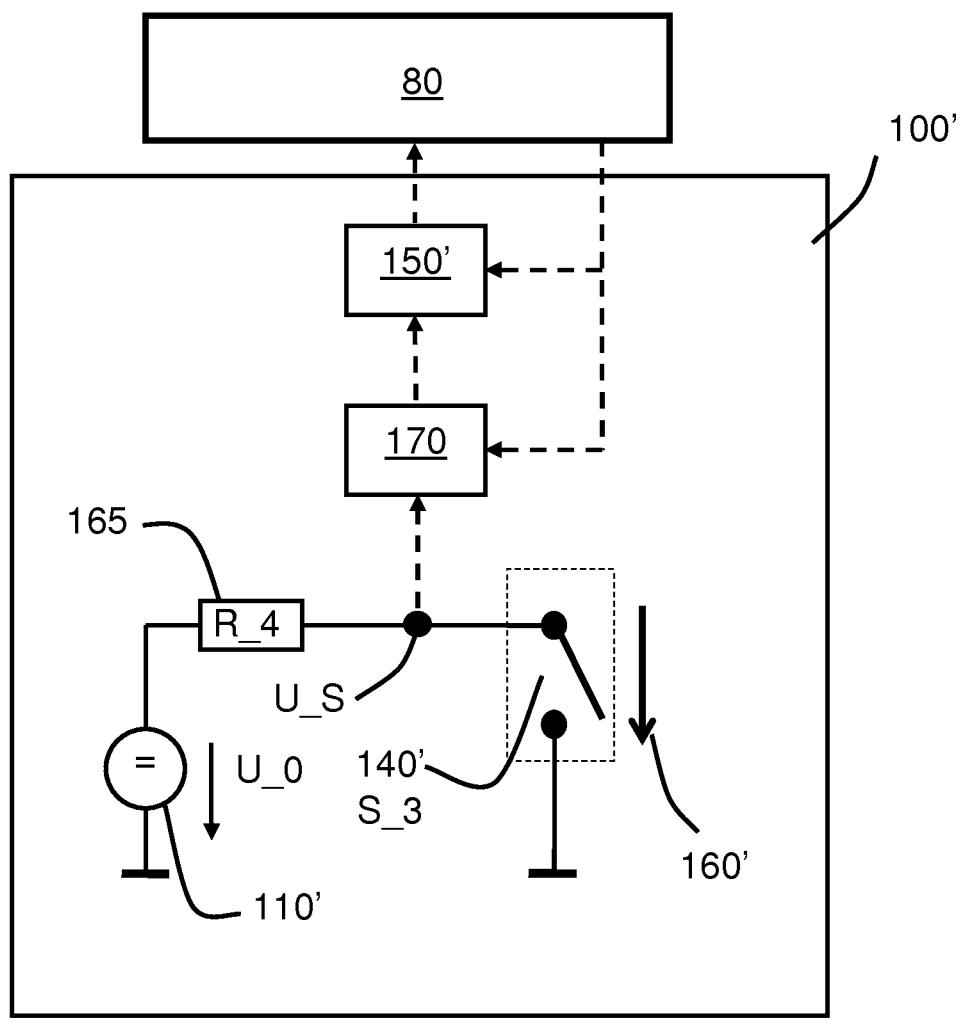
FIG. 5 depicts the schematic structure of a patient state monitor of an exemplary administration device.

FIG. 5 shows the schematic structure of a patient state monitor 100' according to a another exemplary embodiment. For this kind of embodiment, the motion-sensitive sensor unit 140' is a switch which may be both statically open and/or statically closed as long as the patient does not substantially move and may change from 'open' to 'closed' and vice versa due to patient motion. The motion-sensitive sensor unit 140' may especially be a tilt switch which is open or closed in dependence of the orientation of a measurement vector 160' with respect to gravity. The state of the tilt switch 140' makes up the sensor signal (SS).

In addition to the tilt switch 140', the patient state monitor 100' includes a resistor 165 serving as a pull-up resistor, resulting in the switch voltage U\_S being substantially equal to voltage U\_0 110' with respect to ground if the tilt switch 140' is open and to be substantially zero with respect to ground if the tilt switch 140' is closed. The switch voltage U_S makes up the patient state signal (PS) with U_S=U_C representing a Boolean '1' (tilt switch 140' open) and U_S=0 representing a Boolean '0' (tilt switch 140' closed). The patient state monitor 100' further comprises a comparison unit 170, the comparison unit 170 including a two-stage 1 Bit shift register for storing the state of the tilt switch 140' and an XOR-logic. The patient state monitor 100' further includes a counter unit 150'. Even though not explicitly shown in FIG. 5, the patient state monitor 100' may include additional supplementary components such as a Schmitt trigger for converting the switch voltage U_S into a binary signal.

Figure 6:
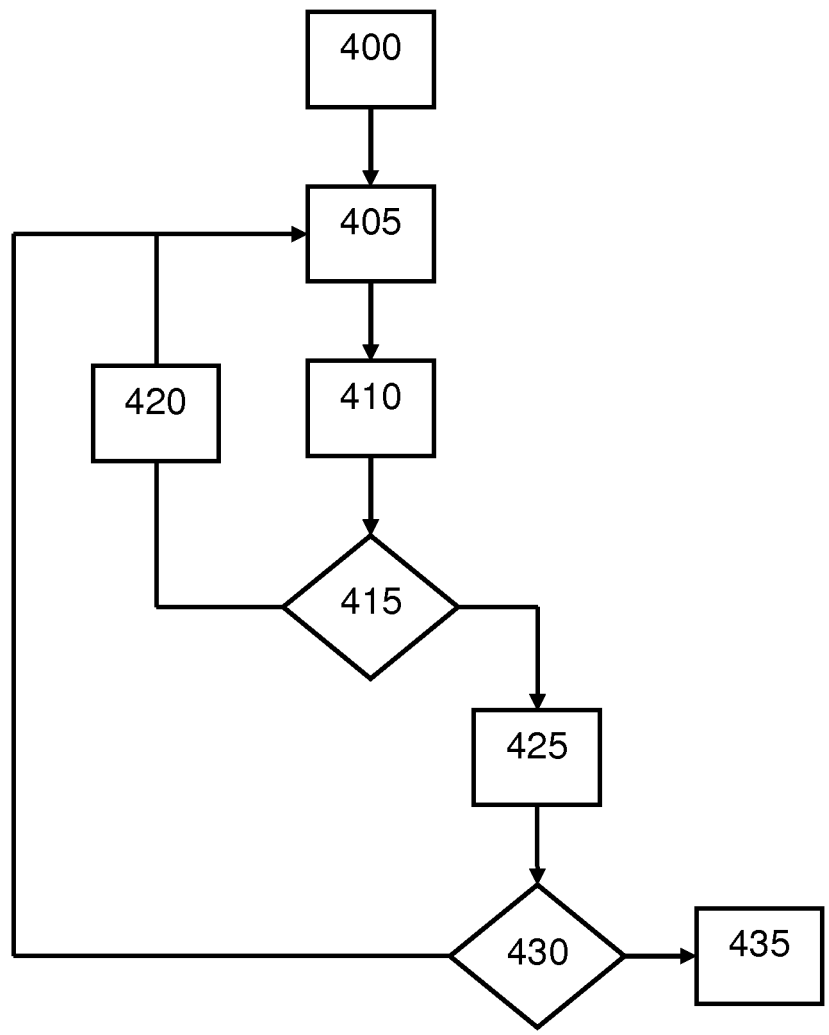
FIG. 6 depicts a flow diagram for the operation of an exemplary patient state monitor according to FIG. 5.

In the following, reference is made to FIG. 5 as well as to the FIG. 6, the flow diagram provided by FIG. 6 representing the operation of the patient state monitor 100'. In block 400, the state of the tilt switch 140' is stored in the first register Reg_1 of the shift register of comparison unit 170. After waiting for a monitoring interval, the monitoring interval having a monitoring interval length MT in block 405, the contents of the first register Reg_1 is shifted to the second register Reg_2 and while the current state of the tilt switch 140' is stored in the first register Reg_1 in step 410.

In block 415, the contents of the first register Reg_1 and the second register Reg_2 are compared by an XOR-Logic included in the comparison unit 170. If the contents of both registers Reg_1 and Reg_2 is different, (for example, either of the registers comprise a 'Boolean 0' while the other of the registers comprises a Boolean '1'), it can be assumed that the patient has moved in the past monitoring interval. In this case, a counter counting the number N of consecutive monitoring intervals without substantial patient motion, the counter being included within the counter unit 150', is reset in block 420 and a new monitoring interval is started with block 405.

If the contents of both registers Reg_1 and Reg_2 is identical, (i.e. both of the registers either comprise a 'Boolean 1' or a 'Boolean 0'), the patient may not have moved within the past monitoring interval, or the patient may have moved such that the state of the tilt switch 140' in block 410 is identical to the state of the tilt switch 140' in block 400. In this case, the counter comprised by the counter unit 150' is incremented by one in block 425 and the counter state N is compared with a threshold number (TN) in block 430 by a comparator included with the counter unit 150'. If the counter state equals the threshold number (TN), an alarm triggering signal is generated by the counter unit 150' and transmitted to the controller unit in block 435. Otherwise a new monitoring interval is started with block 405.

It should be noted that a patient motion within a monitoring interval is not necessarily detected according to this type of exemplary embodiment. In order to prevent the generation of false alarms, it is therefore possible to choose the threshold number (TN) somewhat larger as compared to a design which ensures each patient motion within a monitoring interval to be detected. The threshold number (TN) may be selected such that the probability of only undetected patient motion within TN consecutive monitoring intervals is virtually zero. For example, assuming a monitoring interval length MT of 3 minutes, the threshold number (TN) may be chosen to 40.

Figure 7:
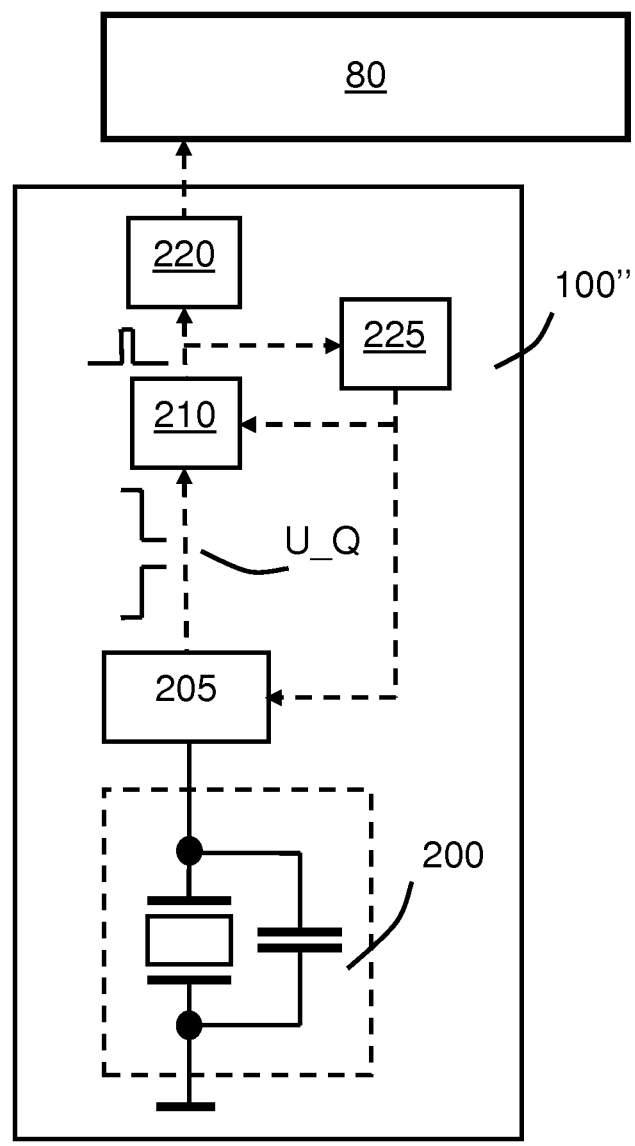
FIG. 7 depicts a schematic structure of a patient state monitor for an exemplary administration device.

FIG. 7 depicts a schematic structure of a patient state monitor 100" according to a another exemplary embodiment. For this kind of embodiment, the motion-sensitive sensor unit is a piezo electric acceleration sensor 200 generating a charge Q when being accelerated, the charge Q being proportional to the acceleration. Following the acceleration sensor 200, the patient state monitor 100" comprises a charge amplifier 205, the charge amplifier 205 converting the charge Q into a charge proportional voltage U_Q. The charge Q makes up the sensor signal (SS). The patient state monitor 100" further includes a pulse former 210, the pulse former 210 generating a triggering pulse upon a falling edge or rising edge of the charge proportional voltage Q_C. The output of the pulse former 210 makes up the patient state signal (PS). The patient state monitor 100" further includes a sampling timer 220, and a hold off-timer 225. The hold-off timer 225 is adapted to selectively energize the charge amplifier 205 and the pulse former 210. Both the sampling timer 220 and the hold-off timer include a timer and a comparator to compare the timer state with a threshold time and to generate an output signal resulting from the comparison. For the sampling timer, the corresponding threshold time is made up by the maximum sampling interval length (ST)_max, for the hold-off timer the corresponding threshold time is made up by the non-sampling interval length NST.

Figure 8:
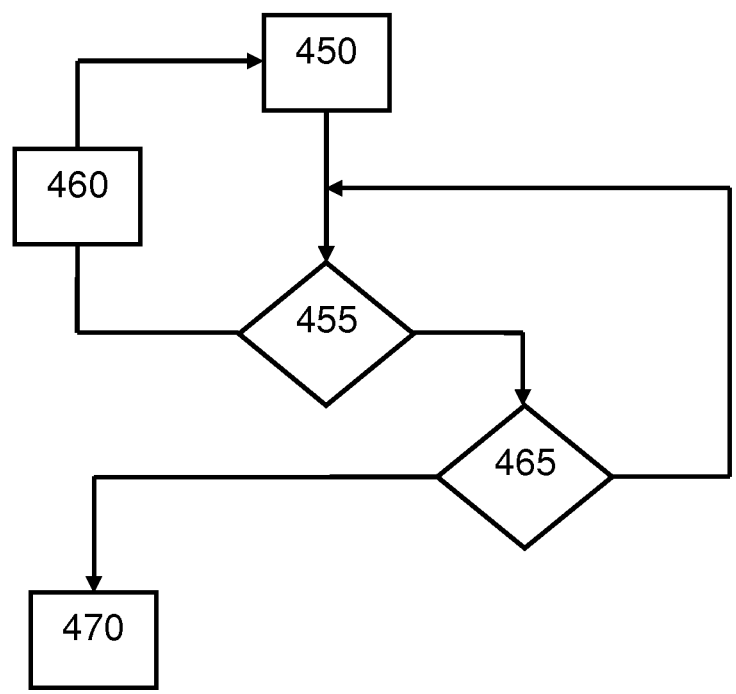
FIG. 8 depicts a flow diagram for the operation of an exemplary patient state monitor according to FIG. 7.

In the following, reference is made to FIG. 7 as well as to FIG. 8. The flow diagram provided by FIG. 8 represents the operation of the patient state monitor 100". In block 450 of FIG. 8, a sampling interval is started by resetting and starting the sampling timer 220, the sampling timer 220 counting the sampling time t. In block 455, the output of the pulse former 210 is sampled. A pulse generated by the pulse former 210 may be indicative for either of a positive or negative pulse of the charge proportional voltage U_Q as a consequence from an acceleration pulse measured by the piezo electric acceleration sensor 200. In this case, the hold-off timer disenergizes the charge amplifier 205 and the pulse former 210 and stops the sampling timer 220, followed by waiting for a non-sampling interval having a non-sampling interval length NST in block 460. At the end of the non-sampling interval, the charge amplifier 205 and the pulse former 205 are reenergized and a new sampling interval is started with block 450.

If no pulse is detected at the output of the pulse former 210 in block 455, the sampling time t as measured by the sampling timer 220 is compared to the maximum sampling interval length (ST)_max in block 465. If the sampling time t equals the maximum sampling interval length (ST)_max, an alarm triggering signal is generated in block 470. Otherwise, the output of the pulse former 210 is sampled again in block 455.

The non sampling interval length NST may be chosen such that at least one patient motion occurs during the sampling interval if the patient is not in a coma. For example, the non-sampling interval length NST may be chosen to be 15 minutes and the maximum sampling interval length (ST)_max may be chosen to be 45 minutes, resulting in an alarming time interval (AT) of 1 hour. The non-sampling interval length NST may further be adaptive and may especially be shorter during night time as compared to daytime or may not be present at all. According to a modification of this exemplary embodiment, the sensor signal is evaluated quantitatively and the patient state signal (PS) is given by the average acceleration level within a sampling interval and the predefined motion level is given by a threshold average acceleration level.

For at least some of the exemplary embodiments, the alarming time interval (AT) is initially set to a long time (for example, 6 hours), according to the configuration of a health care professional. Subsequently, the sensor signal (SS) is processed and evaluated for an adoption time interval of, for example, 1 month, in order to determine the patient's individual motion habits and amount of motion. An appropriate value for the alarming time interval (AT) may subsequently be determined as the longest time interval (LT) without substantial patient motion within the adoption time interval. An additional safety margin is added to this value to make up the alarming time in order avoid false alarms. The safety margin may be a fixed amount of time of (such as 30 minutes), which is added to longest time interval (LT) without substantial patient motion within the adoption time interval or may be defined in dependence of the longest time interval (LT) without substantial patient motion within the adoption time interval by multiplying it with a safety factor of, for example, 1.1, the safety factor being larger than one. Additionally, for at least some of the exemplary embodiments, the alarm triggering signal may further or alternatively be transmitted to a separate user interface, to a cell phone, or the like.

Therefore, at least the following is claimed:

1. An administration device for administration of a liquid drug over an extended time period to a patient, comprising:
   an administration unit;
   a housing that houses the administration unit, the housing being adapted to be carried by the patient over the extended time period;
   a controller unit adapted to control operation of the administration unit, the controller unit further adapted to receive an alarm triggering signal;
   an alarming unit that is coupled to the controller unit, the alarming unit adapted to generate an alarm signal on reception of the alarm triggering signal by the controller unit; and
   a patient state monitor that includes a motion-sensitive sensor unit, the motion-sensitive sensor unit being reactive on patient motion, the patient state monitor being adapted to process a sensor signal (SS) generated by the motion-sensitive sensor unit, and a counter unit adapted to generate the alarm triggering signal and to transmit the alarm triggering signal to the controller unit if processing of the sensor signal (SS) indicates a patient motion level is below a predefined motion level, the predefined motion level being defined by a length of time-periods without patient motion that can be expected for a conscious human.

2. The administration device of claim 1, wherein the motion-sensitive sensor unit is coupled to a motion sensor unit housing, the motion sensor unit housing being separate from the housing.

3. The administration device of claim 1, wherein the motion-sensitive sensor unit includes at least one of the following: a tilt sensor, a vibration sensor, a shock sensor, and an acceleration sensor.

4. The administration device of claim 1, wherein the motion-sensitive sensor unit includes at least one binary switching sensor.

5. The administration device of claim 1, wherein the patient state monitor includes an energy storage, the motion-sensitive sensor unit being adapted to modify an energy (E) stored by the energy storage.

6. The administration device of claim 1, wherein the controller unit is adapted to control the administration unit to stop the drug administration on reception of the alarm triggering signal.

7. The administration device of claim 1, wherein the counter unit is adapted to count a number (N) of consecutive monitoring intervals without substantive patient motion.

8. The administration device of claim 7, wherein the counter unit is further adapted to generate the alarm triggering signal if the number (N) of consecutive monitoring intervals without substantive patient motion equals a threshold number (TN).

9. An administration device for administration of a liquid drug over an extended time period to a patient, comprising:
   an administration unit;
   a housing that houses the administration unit, the housing being adapted to be carried by the patient over the extended time period;
   a controller unit adapted to control operation of the administration unit, the controller unit further adapted to receive an alarm triggering signal;
   an alarming unit that is coupled to the controller unit, the alarming unit adapted to generate an alarm signal on reception of the alarm triggering signal by the controller unit; and
   a patient state monitor that includes an energy storage, a motion-sensitive sensor unit being reactive on patient motion and switchably connected to the energy storage, a voltage threshold detector operably coupled to the energy storage and a counter unit, wherein the patient state monitor being adapted to process a binary output of the voltage threshold detector to the counter unit, such that the counter unit is adapted to count a number (N) of consecutive monitoring intervals without substantial patient motion, compare the number (N) of consecutive monitoring intervals without substantial patient motion with a threshold number (TN), and if a capacitor voltage is below a threshold voltage the counter unit is reset to zero, otherwise the number (N) of consecutive monitoring intervals without substantial patient motion is incremented by one.

10. The administration device of claim 9, wherein the motion-sensitive sensor unit is coupled to a motion sensor unit housing, the motion sensor unit housing being separate from the housing.

11. The administration device of claim 9, wherein the motion-sensitive sensor unit includes at least one binary switching sensor adapted to modify an energy (E) stored by the energy storage when the at least one binary switching sensor is in a closed state.

12. The administration device of claim 9, wherein the energy storage is a capacitor of a capacity (C).

13. The administration device of claim 9, wherein the controller unit is adapted to control the administration unit to stop the drug administration on reception of the alarm triggering signal.

14. The administration device of claim 9, wherein the patient state monitor being further adapted to generate the alarm triggering signal if no patient motion has occurred for the threshold number (TN) based on an alarming time interval (AT) which is given by a product of a monitoring length (MT) and the threshold number (TN).

15. The administration device of claim 14, wherein the counter unit further comprises a comparator, the comparator being adapted to generate the alarm triggering signal to the controller unit.

* * * * *

UNITED STATES PATENT AND TRADEMARK OFFICE
CERTIFICATE OF CORRECTION

PATENT NO. : 9,078,965 B2
APPLICATION NO. : 12/901090
DATED : July 14, 2015
INVENTOR(S) : Wim Vander Helm et al.

It is certified that error appears in the above-identified patent and that said Letters Patent is hereby corrected as shown below:

In The Specification

Col. 1, Line 56,
"prise a 'dead man's control, which automatically triggers the" should read
--prise a 'dead man's' control, which automatically triggers the--;

Col. 3, Line 25,
"physical principle. Accordingly, the sensor signal (SS) may" should read
--physical principles. Accordingly, the sensor signal (SS) may--;

Col. 3, Line 35,
"assessed based on diverse criteria such peak acceleration" should read
--assessed based on diverse criteria such as peak acceleration--;

Col. 3, Line 44,
"the housing is adapted to be carried by a patient over an extend" should read
--the housing is adapted to be carried by a patient over an extended--;

Col. 4, Line 1,
"unit and is adapted to be carried by a patient over an extend" should read
--unit and is adapted to be carried by a patient over an extended--;

Col. 4, Line 25,
"elements such as such as application specific integrated cir-" should read
--elements such as application specific integrated cir- --;

Col. 4, Line 38,
"unit further serves as indication unit for general control and" should read
--unit further serves as an indication unit for general control and--;

Signed and Sealed this
Thirty-first Day of May, 2016

Michelle K. Lee
*Director of the United States Patent and Trademark Office*

Col. 4, Line 41,
"tion device may include and/or coupled to the housing. In" should read
--tion device may be included and/or coupled to the housing. In--;

Col. 4, Line 53,
"tions that can not guaranteed to be accessible in an easy and" should read
--tions that cannot be guaranteed to be accessible in an easy and--;

Col. 4, Line 59,
"energy storages, or the like as described in grater detail below" should read
--energy storages, or the like as described in greater detail below--;

Col. 5, Line 36,
"or closed')." should read
--or 'closed').;

Col. 6, Line 63,
"sensitive senor and signal condition circuitry, while not" should read
--sensitive sensor and signal condition circuitry, while not--;

Col. 7, Line 11,
"senor unit that is reactive on patient motion. Similarly, some" should read
--sensor unit that is reactive on patient motion. Similarly, some--;

Col. 7, Line 24,
"administration device may include a motion-sensitive senor" should read
--administration device may include a motion-sensitive sensor--;

Col. 9, Line 17,
"the patient stat signal at the monitoring points in time." should read
--the patient state signal at the monitoring points in time.--;

Col. 10, Line 23,
"maximum sampling interval length (ST)_max, generating an" should read
--maximum sampling interval length (ST)_max, it generates an--;

Col. 11, Line 16,
"alarming unit 33 in form of a buzzer and a alarming unit 35 in" should read
--alarming unit 33 in the form of a buzzer and an alarming unit 35 in the--;

Col. 11, Line 25
"further serve as alarming unit." should read
--further serve as an alarming unit.--;

CERTIFICATE OF CORRECTION (continued)
U.S. Pat. No. 9,078,965 B2

Col. 12, Line 21,
"that are normally open and close temporarily due to motion," should read
--that are normally opened and close temporarily due to motion,--;

Col. 12, Lines 42-43,
"if it is exposed to an acceleration a in the direction defined by the measurement vector 160, the acceleration a exceeding a" should read
--if it is exposed to an acceleration in the direction defined by the measurement vector 160, the acceleration exceeding a--;

Col. 12, Line 55,
"the patient state signal (PS) is made up be the capacitor" should read
--the patient state signal (PS) is made up by the capacitor--;

Col. 12, Line 63,
"charging resistor 115, resulting the energy (E) stored by the" should read
--charging resistor 115, resulting in the energy (E) stored by the--;

Col. 14, Line 40,
"substantially equal to voltage U_0 nor to substantially equal" should read
--substantially equal to voltage U_0 nor substantially equal--; and Col. 16, Lines 7-8,
"tor 100" further includes a sampling timer 220, and a hold off-timer 225. The hold-off timer 225 is adapted to selectively" should read
--tor 100" further includes a sampling timer 220, and a hold-off timer 225. The hold-off timer 225 is adapted to selectively--.